United States Patent [19]
Kao

[11] 4,138,590

[45] Feb. 6, 1979

[54] PROSTAGLANDIN DERIVATIVES

[75] Inventor: Wenling Kao, King of Prussia, Pa.

[73] Assignee: American Home Products Corporation, New York, N.Y.

[21] Appl. No.: 759,315

[22] Filed: Jan. 13, 1977

[51] Int. Cl.² .......................................... C07C 177/00
[52] U.S. Cl. .................................... 562/503; 542/426; 560/53; 560/121; 562/463; 424/305; 424/308; 424/317
[58] Field of Search ...................... 260/468 D, 514 D; 560/121

[56] References Cited

U.S. PATENT DOCUMENTS

| | | | |
|---|---|---|---|
| 3,954,844 | 5/1976 | Colton et al. | 260/488 |
| 4,016,184 | 5/1977 | Morton | 260/408 |

*Primary Examiner*—Robert Gerstl
*Attorney, Agent, or Firm*—Robert Wiser

[57] ABSTRACT

Derivatives of $PGD_2$ are prepared. These new compounds not heretofore found in nature display pharmacological activity, for example, inhibition of blood platelet aggregation.

2 Claims, 1 Drawing Figure

R' = CH₃    II
R' = C≡CH    III
R' = C₆H₅    IV

R' = CH₃    V
R' = C≡CH    VI
R' = C₆H₅    VII

R' = CH₃    VIII
R' = C≡CH    IX
R' = C₆H₅    X

PROSTAGLANDIN DERIVATIVES

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation and the ability to reduce gastric secretion.

The present invention concerns 9-dehydro-9-deoxy-$PGD_2$ derivatives which, in addition, bear either a methyl, ethynyl, or phenyl substituent at the 9 position (using the prostanoic acid numbering system).

SUMMARY OF THE INVENTION

The invention sought to be patented in its first composition aspect resides in the concept of a chemical compound of the structure:

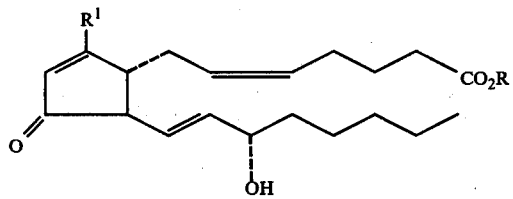

wherein R is hydrogen, alkyl of from 1 to 6 carbon atoms, an alkali metal cation, or a pharmacologically acceptable cation derived from ammonia or a basic amine; and $R^1$ is methyl, ethynyl, or phenyl.

The tangible embodiments of the first composition aspect of the invention possess the inherent general physical properties of being clear to yellow oils, or crystalline solids and when R is hydrogen, are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the first composition aspect of the invention possess the inherent applied use characteristic of retarding blood platelet coagulation as measured by a modification of the procedure of G. V. R. Borin and M. J. Cross, J. Physiol., 168, 178 (1963) infra. In addition, when $R^1$ is methyl, the compositions exert bronchodilating effects in warm-blooded animals, which effects are evidenced by pharmacologic evaluation according to standard test procedures.

The invention sought to be patented in a first specific aspect of the first composition aspect resides in the concept of a chemical compound of the structure:

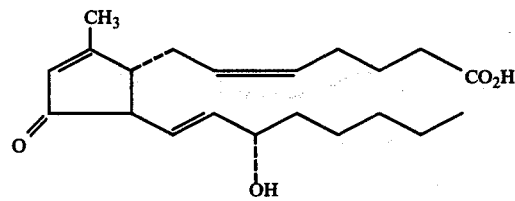

The invention sought to be patented in a second specific aspect of the first composition aspect resides in the concept of a chemical compound of the structure:

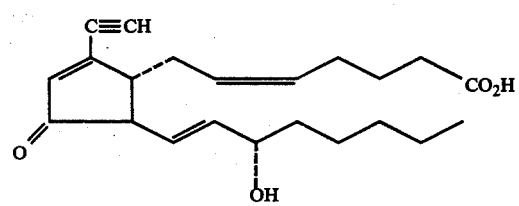

The invention sought to be patented in a third specific aspect of the first composition aspect resides in the concept of a chemical compound of the structure:

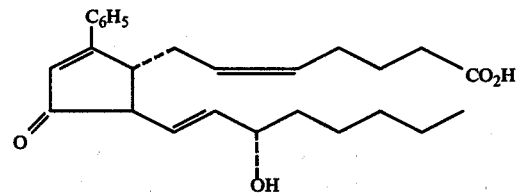

The invention sought to be patented in its second composition aspect resides in the concept of a chemical compound of the structure:

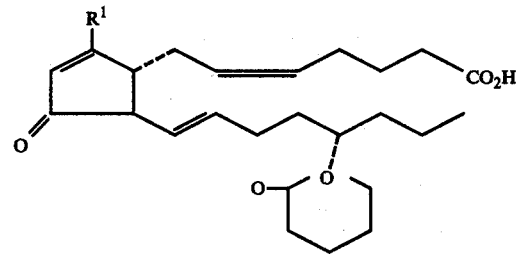

wherein $R^1$ is methyl, ethynyl, or phenyl.

The tangible embodiments of the second composition aspect of the invention possess the inherent general physical properties of being clear to yellow oils, or crystalline solids. They are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of being intermediates for the synthesis of the embodiments of the first composition aspect of the invention.

The invention sought to be patented in a first specific aspect of the second composition aspect resides in the concept of a chemical compound of the structure:

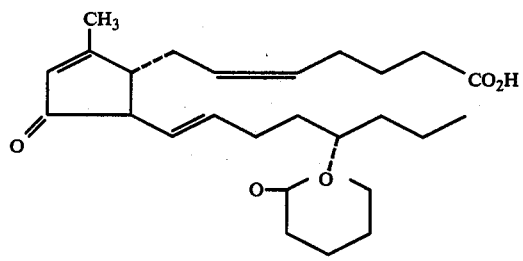

The invention sought to be patented in a second specific aspect of the second composition aspect resides in the concept of a chemical compound of the structure:

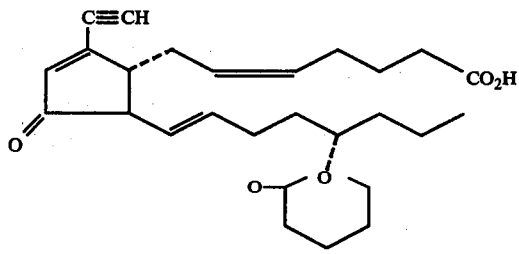

The invention sought to be patented in a third specific aspect of the second composition aspect resides in the concept of a chemical compound of the structure:

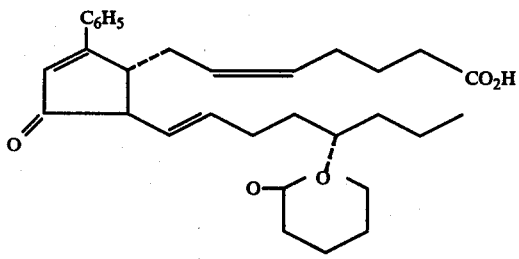

The invention sought to be patented in its third composition aspect resides in the concept of a chemical compound of the structure:

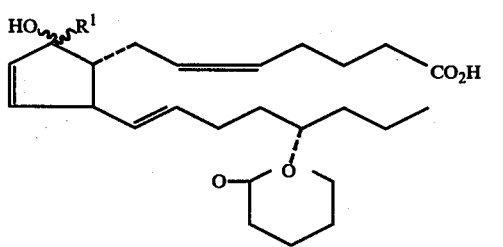

wherein $R^1$ is methyl, ethynyl, or phenyl.

The tangible embodiments of the third composition aspect of the invention possess the inherent general physical properties of being clear to yellow oils, or crystalline solids. They are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodimdents of the third composition aspect of the invention possess the inherent applied use characteristic of being intermediates for the synthesis of the embodiments of the first composition aspect of the invention.

The invention sought to be patented in a first specific aspect of the third composition aspect resides in the concept of a chemical compound of the structure:

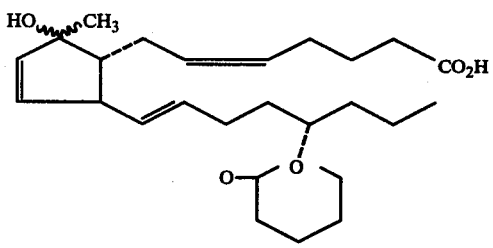

The invention sought to be patented in a second specific aspect of the third composition aspect resides in the concept of a chemical compound of the structure:

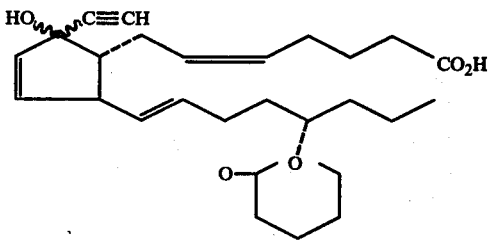

The invention sought to be patented in a third specific aspect of the third composition aspect resides in the concept of a chemical compound of the structure:

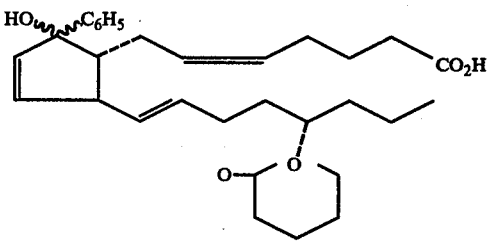

DESCRIPTION OF THE PREFERRED EMBODIMENTS

Figure 1:
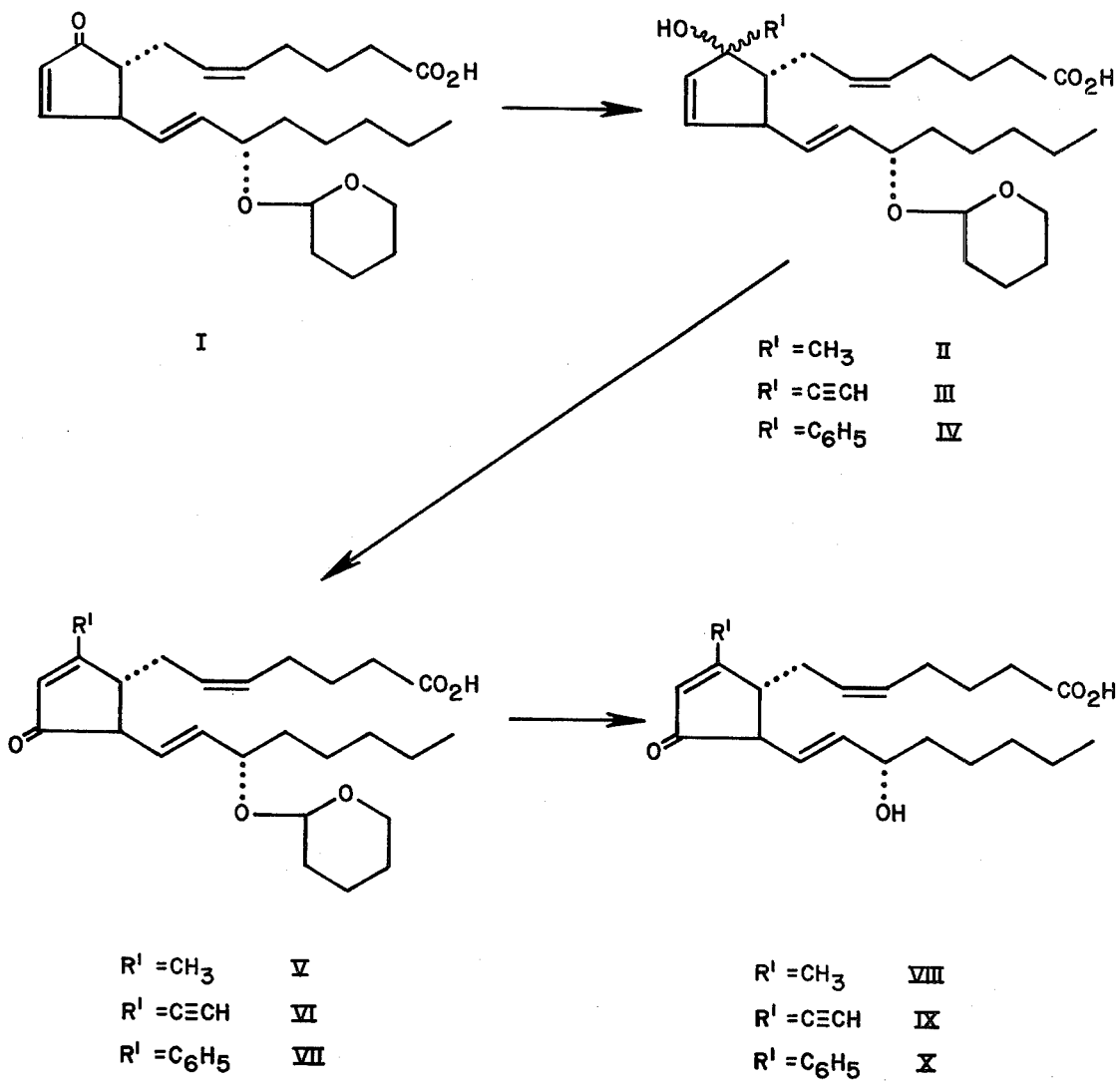

In describing the synthesis of the compositions of the invention, reference will be made to FIG. I, wherein is illustrated the preparation of specific embodiments of the invention, and wherein the formulae representing the various aspect of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of paper, when a dashed line (--) is used, the substituent will be understood to be in the α (down) configuration; and where a heavy line (▶) is used, the substituent will be understood to be in the β (up) configuration; and when a wavy line (∼) is used both α and β configurations are contemplated for the substituent. Thus, for example, when a new assymetric center is created by a below-described reaction, for example the addition of a Grignard reagent to a ketone, since both possible configurations for the new substituents will be produced they will be denoted by wavy lines (∼). Both of said isomers, unless otherwise noted, are considered to be full equivalents for the purposes of this invention. The formulae in FIG. I are free carboxylic acids. It will be obvious to those skilled in the art that the free acids may readily be treated to produce conventional alkyl esters as for example, with diazomethane, or with an alkanol and the proper catalyst, or the free acids may be converted to an alkali metal or basic amine salt. The esters, salts and free acids are considered to be full equivalents for the purposes of the invention. Finally, the use of specific embodiments in FIG. I to illustrate the invention is merely descriptive and is not intended to delimit the scope of the invention.

Referring now to FIG. I, the 15-tetrahydropyranyl derivative of PGA$_2$, compound I, is readily prepared from, for example, PGA$_2$ itself, which preparation is described in Belgian Pat. No. 803,854. Compound I is treated with a Grignard reagent, for example, methyl magnesium bromide, ethynyl magnesium bromide, or phenyl magnesium bromide, or their respective equivalents, for example, methyl magnesium iodide, ethynyl magnesium oxide, or phenyl magnesium iodide; producing respectively, compounds II, III, and IV. These allylic alcohols are next oxidized with, for example, chromium trioxide in 5% sulfuric acid producing, respectively, the unsaturated ketones, V, VI and VII, which upon mild acidic hydrolysis (e.g. 65% acetic acid/40° C.) yield respectively, the de-protected alcohols VIII, IX, and X.

When used herein and in the appended claims, the term "alkali metal" includes, for example, sodium, potassium, lithium, and the like. A "pharmacologically acceptable cation derived from ammonia or a basic amine" contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

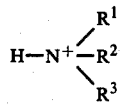

wherein $R^1$, $R^2$, and $R^3$, independently, are hydrogen, alkyl of from 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms or, when taken together with the nitrogen atom to which they are attached, any two of $R^1$, $R^2$, and $R^3$ form part of a 5 to 6-membered heterocyclic ring containing carbon, hydrogen, oxygen, nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and tri-methyl-ammonium, mono-, di-, and tri-ethylammonium, mono-, di-, and tri-propylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and tri-ethanolammonium, ethyldiethanolammonium, n-butylmonoethanolammonium, tris-(hydroxymethyl)methylammonium, phenylmonoethanolammonium, and the like.

The following examples further illustrate the best mode contemplated by the inventor for the practice of the invention.

EXAMPLE 1

7-{5-Hydroxy-5-Methyl-2β-[(3S)-3-(Tetrahydropyran-2-yloxy)-trans-1-Octenyl]-3-Cyclopenten-1α-yl}-cis-5-Heptenoic Acid II An ice-cooled solution of 11.5 g. of 7-{5-oxo-2β-[(3S)-3-(tetrahydropyran-2-yloxy)trans-1-octenyl]-3-cyclopenten-1α-yl}-cis-5-heptenoic acid in 350 ml. of THF was treated with 36 ml. of 2M methyl magnesium bromide and stirred at 0° C. for two and a half hours. The mixture was treated with aqueous ammonium chloride solution and diluted with ether. After washing with water and drying with magnesium sulfate, the ether solution was evaporated and the residue chromatographed on silica gel. Elution with 35% ethyl acetate in hexane afforded 8.2 g. of 7-{5-hydroxy-5-methyl-2β-[(3S)-3-(tetrahydropyran-2-yloxy)-trans-1-octenyl]-3-cyclopenten-1α-yl}-cis-5-heptenoic acid as an oil, $\lambda_{max}^{film}$ 3.0, 3.4, 5.75 (shoulder), 5.84, 6.9, 7.3, 8.12, 9.05, 9.82 and 10.26μ.

NMR Analysis: δ 6.04 (s, 2, OH), 5.0–5.8 (m, 6, olefinic H), 4.65 (s, 1,

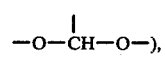

3.7–4.25 (m, 2, —O-CH$_2$-), 1.2 (s, C$_9$-methyl) and 0.91 (t, 3, C$_{20}$-methyl)ppm.

Mass Spectral Analysis: M$^+$-THP at m/e 277 (theory 277).

EXAMPLE 2

7-{5-Hydroxy-5-Ethynyl-2β-[(3S)-3-(Tetrahydropyran-2-yloxy)-trans-1-Octenyl]-3-Cyclopenten-1α-yl}-cis-5-Heptenoic Acid III Treatment of compound I as in Example 1 but substituting ethynyl magnesium bromide for methyl magnesium bromide produces 7-{5-hydroxy-5-ethynyl-2β-[(3S)-3-(tetrahydropyran-2-yloxy)-trans-1-octenyl]-3-cyclopenten-1αyl}-cis-5-heptenoic acid.

EXAMPLE 3

7-{5-Hydroxy-5-Phenyl-2β-[(3S)-3-(Tetrahydropyran-2-yloxy)-trans-1-Octenyl]-3-Cyclopenten-1α-yl}-cis-5-Heptenoic acid IV Treatment of compound I as in Example 1 but substituting phenyl magnesium bromide for methyl magnesium bromide produces 7-{5-hydroxy-5-phenyl-2β-[(3S)-3(tetrahydropyran-2-yloxy)-trans-1-octenyl]-3-cyclopenten-1α-yl}-cis-5-heptenoic acid.

EXAMPLE 4

7-{2-Methyl-4-Oxo-5β-[(3S)-3-Tetrahydropyran-2-yloxy)-trans-1-Octenyl]-2-Cyclopenten-1α-yl}-cis-5-Heptenoic Acid V An ice-cooled solution of 3.6 g. of 7-{5-hydroxy-5-methyl-2β-[(3S)-3-(tetrahydropyran-2-yloxy)-trans-1-octenyl]-3-cyclopenten-1α-yl}-cis-5-heptenoic acid in 90 ml. of ether was treated with 1.0 g. chromium trioxide in 10 ml. of 5% aqueous sulfuric acid solution. After stirring at 0° for 1 hour, the mixture was diluted with ether, washed with water and dried. Solvent was evaporated and the residue chromatographed on silica gel. Elution with 20% ethyl acetate in hexane afforded 1.6 g. of 7-{2-methyl-4-oxo-5β-[(3S)-3-tetrahydropyran-2-yloxy)-trans-1-octenyl]-2-cyclopenten-1α-yl}-cis-5-heptenoic acid as an oil, $\lambda_{max}^{film}$ 3.0 (shoulder), 3.4, 5.75 (shoulder), 5.85, 6.16, 6.97, 7.28, 8.37, 8.90, 9.02, 9.3, 9.8, 10.24, 11.1 and 11.55 μ.

NMR Analysis: δ9.0–9.6 (m, 1, OH), 6.03 (s, 1, $C_{10}$-H) and —O-$CH_2$—), 2.8 (m, 2, $C_8$ and $C_{12}$-H), 2.17 (s, $C_9$-methyl) and 0.94 (t, 3, $C_{20}$-methyl) ppm.

Mass Spectral Analysis: M$^+$ -OTHP at m/e 331 (theory 331).

UV Spectrum: $\lambda_{max}^{EtOH}$ 225 mμ(ε 11,680).

EXAMPLE 5

7-{2-Ethynyl-4Oxo-5β-[(3S)-3-Tetrahydropyran-2-yloxy)-trans-1-Octenyl]-2-Cyclopenten-1α-yl}-cis-5-Heptenoic Acid VI Oxidation of the compound produced in Example 2 by a procedure substantially identical to that described in Example 4 produces 7-{2-ethynyl-4-oxo-5β-[(3S)-3-tetrahydropyran-2-yloxy)-trans-1-octenyl]-2-cyclopenten-1α-yl}-cis-5-heptenoic acid.

EXAMPLE 6

7-{2-Phenyl-4-Oxo-5β-[(3S)-3-Tetrahydropyran-2-yloxy)-trans-1-Octenyl]-2-Cyclopenten-1α-yl}-cis-5-Heptenoic Acid VII Oxidation of the compound produced in Example 3 by a procedure substantially identical to that described in Example 4 produces 7-{2-phenyl-4-oxo-5β-[(3S)-3-tetrahydropyran-2-yloxy)-trans-1-octenyl]-2-cyclopenten-1α-yl}-cis-5-heptenoic acid.

EXAMPLE 7

7-{5β-[(3S)-3-Hydroxy-trans-1-Octenyl]-2-Methyl-4-Oxo-2-Cyclopenten-1α-yl}-cis-5-Heptenoic Acid VIII A solution of 1.5 g. of 7-{2-methyl-4-oxo-5β-[(3S)-3-(tetrahydropyran-2-yloxy)-trans-1-octenyl]-2-cyclopenten-1α-yl}-cis-5-heptenoic acid in a mixture of water-acetic acid (5 ml. :10 ml.) and stirred at 40° for 3 hours. Solvents were evaporated and the residue chromatographed on silica gel. Elution with 35% ethyl acetate in hexane afforded 0.75 g. of 7-{5β-[(3S)-3-hydroxy-trans-1-octenyl]-2-methyl-4-oxo-2-cyclopenten-1α-yl}-cis-5-heptenoic acid as an oil, $\lambda_{max}^{film}$ 3.0 (shoulder), 3.4, 5.75 (shoulder), 5.85, 6.15, 7.0, 7.25, 7.7, 8.54 and 10.37μ.

NMR Analysis: δ 6.59 (s, 2, OH), 6.07 (s, 1, $C_{10}$—H), 5.10–5.87 (m, 4, olefinic H), 4.18 (m, 1, $C_{15}$-H), 2.8 (m, 2, $C_8$ & $C_{12}$-H), 2.17 (s, $C_9$-methyl) and 0.91 (t, 3, $C_{20}$-methyl) ppm.

Mass Spectral Analysis: M$^+$ -$H_2O$ at m/e 330.2169 (theory 330.2195).

UV Spectrum: $\lambda_{max}^{EtOH}$ 226 mμ (ε 11,120).

EXAMPLE 8

7-{5β-[(3S)-3-Hydroxy-trans-1-Octenyl]-2-Ethynyl-4-Oxo-2-Cyclopenten-1α-yl}-cis-5-Heptenoic Acid IX A solution of 1.3 g. of 7-{2-ethynyl-4-oxo-5β-[(3S)-3-(tetrahydropyran-2-yloxy)-trans-1-octenyl]-2-cyclopenten-1α-yl}-cis-5-heptenoic acid in a mixture of water-acetic acid (8 ml. :16 ml.), and stirred at 45° for 3½ hours. Solvents were evaporated and the rate chromatographed on silica gel. Elution with 30% ethyl acetate in hexanes afforded 0.45 g. of 7-{5β-[(3S)-3-hydroxy-trans-1-octenyl]-2-ethynyl-4-oxo-2-cyclopenten-1α-yl}-cis-5-heptenoic acid as an oil, $\lambda_{max}^{film}$ 2.9 (shoulder), 3.1, 3.4, 4.8, 5.8 (shoulder), 5.87, 6.3, 7.1, 8.1, 8.6 and 10.36μ.

NMR Analysis: δ6.67 (s, 2, OH), 6.4 (s, 1, =CH-C=O), 5.5–5.75 (m, 4, olefinic), 4.20 (m, 1, $C_{15}$-H), 4.04 (s, L, HC≡CH-C≡C), 2.9 (m, 2, $C_8$ and $C_9$-H) and 0.92 (5, 3, -$CH_3$) ppm.

Mass Spectral Analysis: M$^+$ -$H_2O$ at m/e 340 (theory 340).

UV Spectrum: $\lambda_{max}^{EtOH}$ 260 mμ (ε 13,400).

EXAMPLE 9

7-{2β-[(3S)-3-Hydroxy-trans-1-Octenyl]-3-Oxo-5-Phenyl-4-Cyclopenten-1α-yl}-cis-5-Heptenoic Acid X A solution of 0.7 g. of 7-{4-oxo-2-phenyl-5β-[(3S)-3-(tetrahydropyran-2-yloxy)-trans-1-octenyl]-2-cyclopenten-1α-yl}-cis-5-heptenoic acid in a mixture of water-acetic acid (4 ml. :8 ml.) and stirred at 40° for 3 hours. Solvents were evaporated and the residue chromatographed on silica gel. Elution with 30% ethyl acetate in hexane gave 0.2 g. of 7-{2β-[(3S)-3-hydroxy-trans-1-octenyl]-3-oxo-5-phenyl-4-cyclopenten-1α-yl}-cis-5-heptenoic acid as an oil, $\lambda_{max}^{film}$ 3.0, 3.45, 5.85 (shoulder), 5.95, 6.3, 6.4, 6.75, 6.95, 8.5, 9.8, 10.38, 11.65, 13.0 and 14.5μ.

NMR Analysis: δ 7.54 (s, 5, aromatic), 6.43 (s, 1, =CH-C=O), 6.26 (m, 2, OH), 5.75 (m, 2, $C_{13}$ and $C_{14}$-H), 5.38 (m, 2, $C_5$ and $C_6$-H), 4.19 (m, 1, $C_{15}$-H) and 9.0 (t, 3, -$CH_3$) ppm.

Mass Spectral Analysis: M$^+$ -$H_2O$ at m/e 392 (theory 392).

UV Spectrum: $\lambda_{max}^{EtOH}$ 289 mμ (ε 15,000).

EXAMPLE 10

Evaluation of Bronchodilator Activity

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.15 micrograms to about 25 micrograms, and preferably from about 0.15 to about 15 micrograms. The bronchodilation produced upon aerosol inhalation can be observed by the method of Rosenthale et al., J. Pharmacol. Exp. Ther., 178, 541 (1971). Using this procedure the following results were obtained:

| Compound | Dose (μg) | % Inhibition of the Bronchoconstricting effects of a standard dose* of acetylcholine |
|---|---|---|
| 7-{5β-[(3S)-3-hydroxy-trans-1-octenyl]-2-methyl-4-oxo-2-cyclopenten-1α-yl}-cis-5-heptenoic acid | 1.5<br>15 | 36<br>78 |

*The dose (i.v.) of acetylcholine which produces a ca. 30% bronchoconstriction.

EXAMPLE 11

Blood Platelet Aggregation

Reference: Modification of Born, G.V.R., and Cross, M. J., J. Physiol., 168, 178-195 (1963).
Test Object: Human blood platelets.
Procedure: Platelet aggregation is the initial step in thrombus formation and it is considered that compounds which prevent aggregation or reduce platelet adhesiveness may inhibit the initiation of the arteriosclerotic process. The effect of drugs on aggregation is measured in platelet rich plasma (PRP) containing adenosine diphosphate (ADP) which markedly increases aggregation in vitro and may be a physiological agent for doing so in vivo.

Human blood is collected from fasted normal blood donors in siliconized 50 ml. Vacutainers that contain 3.8% sodium citrate. Centrifugation at 500 g. for 3 minutes at 5° C. separates the red blood cells from the PRP. The supernatant PRP is pipetted off and the remainder is centrifuged at 1000 g. for 10 minutes at 25° C. to obtain platelet poor plasma for standarization of the automated Payton aggregometer. In the running of the platelet aggregation test a cell containing 1.0 ml. of PRP is stirred at 1,100 rpm and the test compound is added in 0.2 ml. of buffered saline to give an initial concentration of $5 \times 10^{-3}$M, or $5 \times 10^{-4}$M. After 3 minutes, a concentration of ADP predetermined to yield marked platelet aggregation (2 to 4 μM) is added in 0.1 ml. of buffered saline. The curve of light transmission at 610 mμ is followed for 6 minutes. Compounds found to be active at the initial concentration are run at lower concentrations.

Standard Compound: 2-4 μM ADP-Reference Compound.

| Compound | Concentration (M) | % Inhibition of ADP Induced Aggregation |
|---|---|---|
| 7-{5β-[(3S)-3-hydroxy-trans-1-octenyl]-2-methyl-4-oxo-2-cyclopenten-1α-yl}-cis-5-heptenoic acid | $5.7 \times 10^{-9}$ | 56 |
| 7-{5β-[(3S)-3-hydroxy-trans-1-octenyl]-2-ethynyl-4-oxo-2-cyclopenten-1α-yl}-cis-5-heptenoic acid | $2.2 \times 10^{-5}$ | 36 |
| 7-{2β-[(3S)-3-hydroxy-trans-1-octenyl]-3-oxo-5-phenyl-4-cyclopenten-1α-yl}-cis-5-heptenoic acid | $1.8 \times 10^{-5}$ | 22 |

The subject matter which the Applicant regards as his invention is particularly pointed out and distinctly claimed as follows:

1. A chemical compound of the structure:

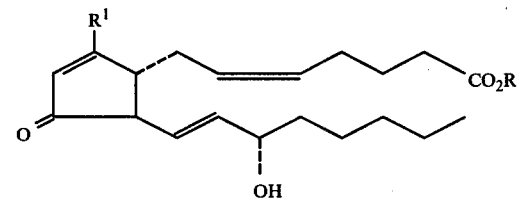

wherein R is hydrogen, alkyl of from 1-6 carbon atoms, alkali metal, or a pharmacologically acceptable cation derived from ammonia or a basic amine; and $R^1$ is ethynyl.

2. The chemical compound of claim 1 wherein R is hydrogen and $R^1$ is ethynyl.

* * * * *